United States Patent [19]

Espinosa

[11] Plant 5,136

[45] Nov. 8, 1983

[54] CORTADERIA 'MONVIN'

[75] Inventor: Gavin Espinosa, Azusa, Calif.

[73] Assignee: Monrovia Nursery Company, Azusa, Calif.

[21] Appl. No.: 341,550

[22] Filed: Jan. 21, 1982

[51] Int. Cl.[3] ..... A01H 5/00
[52] U.S. Cl. ..... Plt./89
[58] Field of Search ..... Plt./89

*Primary Examiner*—Robert E. Bagwill

[57] ABSTRACT

A new and distinct selection of *Cortaderia selloana* (popularly known as pampas grass) and referred to as *Cortaderia selloana* 'Monvin'. A selection with important characteristics of a green and yellow variegation pattern throughout its leaves and possessing a more dwarf overall height and slower growth than the unselected *Cortaderia selloana.* Another distinguishing character of *Cortaderia selloana* 'Monvin' are the strictly female inflorescences which are more showy than the male inflorescences that could be found on seedlings.

2 Drawing Figures

DISCOVERY

This invention relates to a new and distinct selection of *Cortaderia selloana,* a member of the grass family, Gramineae, of the tribe, Arundineae. This new selection was discovered as a chance seedling in a bed of green, non-variegated *Cortaderia selloana* by Gavin Espinosa at Monrovia Nursery Company, 18331 E. Foothill Boulevard, Azusa, Calif. in June of 1977.

The plant to date is known to exist only within the boundaries of Monrovia Nursery and has not been offered for sale or described in any publication.

REPRODUCTION

This new selection has been strictly asexually reproduced at Monrovia Nursery in order to retain the characteristics of leaf variegation, dwarfness and female inflorescences which make this new selection different from the parent. Sexual reproduction, such as seed propagation, could result in a potential loss of the selected attributes. Therefore, sexual reproduction is prohibited and propagation is restricted to asexual reproduction by division. Seed progeny from the new selection has not been observed.

CHARACTERISTICS

*Cortaderia selloana* 'Monvin' differs from other seedlings of *Cortaderia selloana* by its leaf color that is not completely green but rather has a mixture of stripes of yellow and green that run longitudinally the entire length of the leaf. (See illustration—FIG. 1)

This new selection also differs from other seedling *Cortaderia selloana* plants in its more dwarf habit, approximately half to three-fourths the size of the normal green *Cortaderia selloana.*

A third attribute of this new clone selection is the certainty the inflorescences will be female. Female inflorescences produce long silky hairs (otherwise absent on male plants) on a particular part of the flower structure, which make the plume-like inflorescences much more attractive. (See illustration—FIG. 2)

Our new plant was deliberately selected for its unique leaf color variegation, more dwarf growth habit and silky female inflorescences which make for a more desirable plant for ornamental landscape use.

DESCRIPTION:

Below is a detailed description of the new variety, all color terminology is from The British Horticultural Color Charts.

Overall size and habit: Expected size to be approximately fifty inches in height, from ground to tip of inflorescence. Habit is a large densely tufted tussock forming, evergreen perennial.

Leaf blade:

- *Length.*—From tip of leaf to junction of leaf sheath varying from forty to thirty-one inches.
- *Width.*—At basal portion of leaf one-half to five-eighths inch narrowing to one-sixteenth of an inch at leaf tip.
- *Margins.*—Sharply serrulate with tips pointing in a forward direction.
- *Ligule hairs.*—Dense tuft of silky hairs one-eighth inch in length.
- *Color.*—Outer edge of leaf surface: 0960/3 Spinach Green. Center leaf surface: 503/2 Barium Yellow.
- *Pattern color.*—Upper leaf surface: Variegation always in a longitudinal pattern. Spinach Green always on the margins, covering a minimum of half of the outer leaf surface. Barium Yellow is found in the center of the leaf. Thin longitudinal lines of these two colors are present in the remaining leaf surface area. Lower leaf surface: Spinach Green margins and Barium Yellow center appear and gradually blend together as the thin longitudinal lines on the upper surface are not prominent on the lower leaf surface.

Inflorescence:

- *Panicle.*—Twelve inches in length, plume-like, female, silvery white.
- *Spikelets.*—Several flowered.
- *Rachilla.*—Internodes jointed.
- *Glumes.*—Longer than lower florets, one nerved.
- *Lemma.*—With long silky hairs on back and base.

Fruit: Caryopsis enclosed by the lemma and palea.

I claim:

1. A new and distinct *Cortaderia selloana* as substantially shown and described herein, that is a superior selection characterized by a unique leaf variegation pattern, a more dwarf-like plant and a female clone which can be relied upon to produce a more showy plume-like inflorescence.

* * * * *

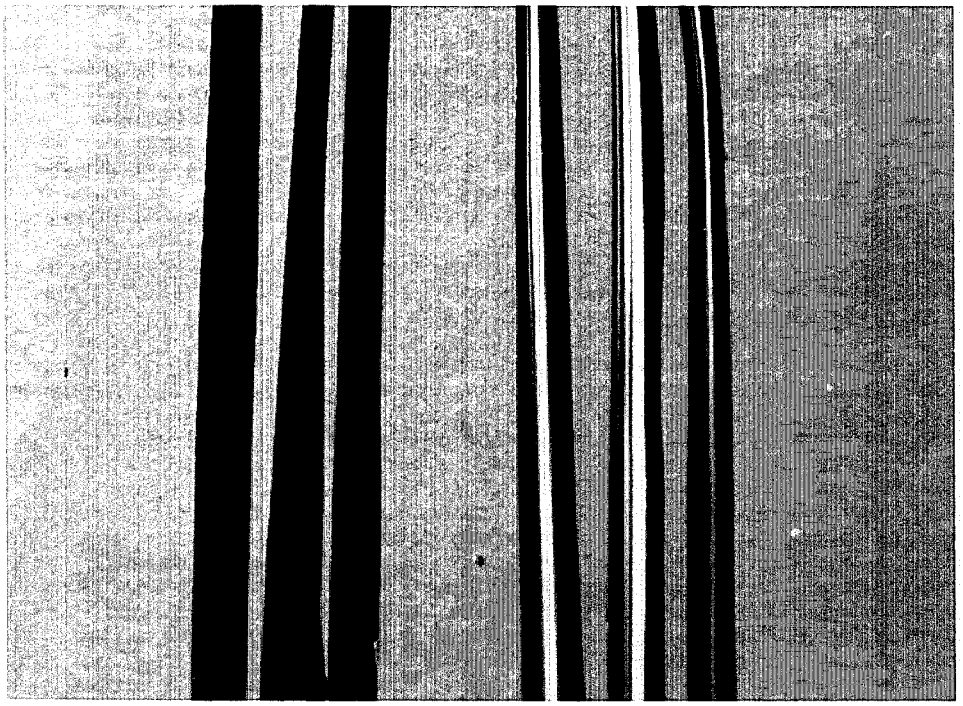
PRIOR ART SELECTION FIG. 1
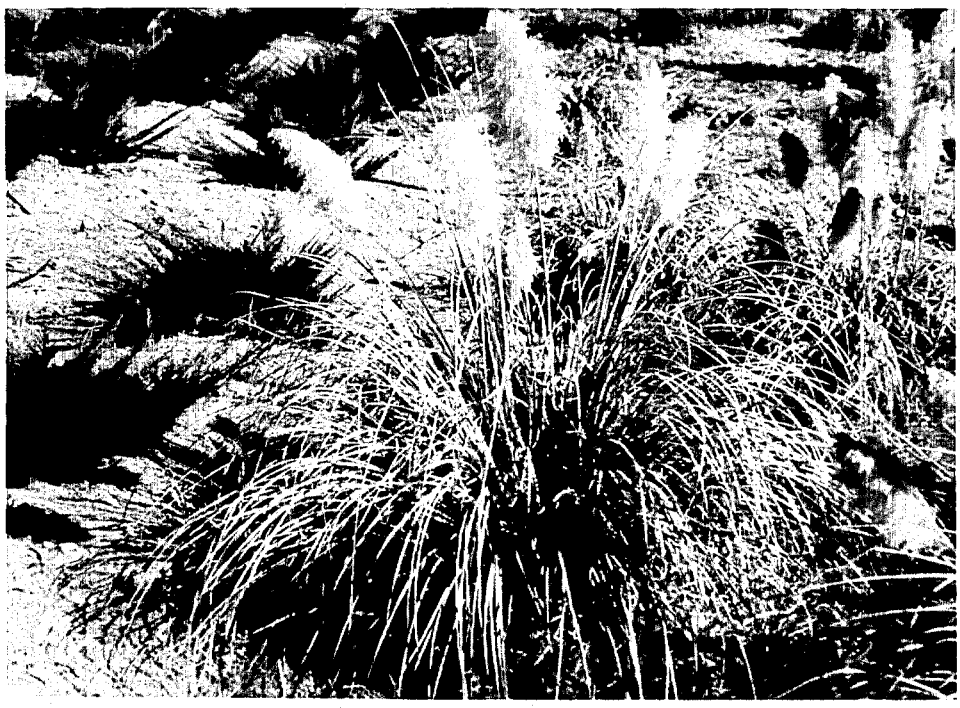
SELECTION FIG. 2